United States Patent
Boloor et al.

(10) Patent No.: US 10,311,206 B2
(45) Date of Patent: *Jun. 4, 2019

(54) ELECTRONIC MEDICAL RECORD SUMMARY AND PRESENTATION

(71) Applicant: International Business Machines Corporation, Armonk, NY (US)

(72) Inventors: Keerthana Boloor, Elmsford, NY (US); Murthy V. Devarakonda, Peekskill, NY (US); Ching-Huei Tsou, Briarcliff Manor, NY (US); Dongyang Zhang, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 1007 days.

This patent is subject to a terminal disclaimer.

(21) Appl. No.: 14/309,058

(22) Filed: Jun. 19, 2014

(65) Prior Publication Data

US 2015/0370979 A1    Dec. 24, 2015

(51) Int. Cl.
| | |
|---|---|
| *G06F 19/00* | (2018.01) |
| *G16H 10/20* | (2018.01) |
| *G16H 10/60* | (2018.01) |
| *G16H 50/20* | (2018.01) |
| *G16H 15/00* | (2018.01) |

(52) U.S. Cl.
CPC .......... *G06F 19/325* (2013.01); *G16H 10/20* (2018.01); *G16H 10/60* (2018.01); *G16H 15/00* (2018.01); *G16H 50/20* (2018.01)

(58) Field of Classification Search
CPC .......................................... G06Q 50/22–50/24
See application file for complete search history.

(56) References Cited

U.S. PATENT DOCUMENTS

| | | | |
|---|---|---|---|
| 7,958,067 B2 | 6/2011 | Schmidtler et al. | |
| 8,856,156 B1 * | 10/2014 | McNair | G06F 17/30734 |
| | | | 707/602 |
| 10,133,847 B2 * | 11/2018 | Devarakonda | G06F 19/00 |
| 2005/0288967 A1 | 12/2005 | Zammit | |
| 2008/0104032 A1 | 5/2008 | Sarkar | |
| 2008/0201280 A1 | 8/2008 | Martin et al. | |
| 2008/0294459 A1 | 11/2008 | Angell et al. | |
| 2009/0080408 A1 | 3/2009 | Natoli et al. | |

(Continued)

OTHER PUBLICATIONS

Voll, K. D. (2006). A methodology of error detection: Improving speech recognition in radiology (Order No. NR23903). Available from ProQuest Dissertations & Theses Global; SciTech Premium Collection. (304944783). Retrieved from https://search.proquest.com/docview/304944783?accountid=14753 (Year: 2006).*

(Continued)

*Primary Examiner* — Robert A Sorey
(74) *Attorney, Agent, or Firm* — Gibb & Riley, LLC

(57) ABSTRACT

Methods, devices, and systems (for outputting a case summary) receive an electronic medical record (EMR) for the medical patient, extract medical data from the EMR, provide a list of medical problems relevant to the EMR, identifying relations between the medical problems and the medical data using a question-answering (QA) system, and output the clinical summary for the EMR. The clinical summary comprises the list of medical problems, the medical data, and the relations.

17 Claims, 13 Drawing Sheets

(56) References Cited

U.S. PATENT DOCUMENTS

| | | | |
|---|---|---|---|
| 2009/0292557 A1 | 11/2009 | Sirohey et al. | |
| 2010/0281025 A1 | 11/2010 | Tsatsou et al. | |
| 2011/0208822 A1* | 8/2011 | Rathod | G06Q 30/02 709/206 |
| 2011/0270630 A1 | 11/2011 | Green, III et al. | |
| 2012/0035959 A1* | 2/2012 | Berdia | G06F 19/325 705/3 |
| 2012/0041911 A1* | 2/2012 | Pestian | G06N 99/005 706/12 |
| 2012/0060216 A1 | 3/2012 | Chaudhri et al. | |
| 2012/0173279 A1 | 7/2012 | Nessa et al. | |
| 2012/0265788 A1 | 10/2012 | Naeymi-Rad et al. | |
| 2013/0054589 A1 | 2/2013 | Cheslow | |
| 2013/0124523 A1* | 5/2013 | Rogers | G06F 19/32 707/737 |
| 2013/0124960 A1 | 5/2013 | Velingkar et al. | |
| 2013/0132308 A1* | 5/2013 | Boss | G06F 17/30976 706/12 |
| 2013/0173657 A1 | 7/2013 | James et al. | |
| 2013/0218596 A1* | 8/2013 | Gome | G06Q 10/06 705/3 |
| 2013/0262357 A1* | 10/2013 | Amarasingham | G06F 19/00 706/21 |
| 2014/0046697 A1* | 2/2014 | Rogers | G06F 19/327 705/3 |
| 2014/0317080 A1* | 10/2014 | Piraino | G16H 10/60 707/706 |
| 2015/0294088 A1* | 10/2015 | Walker | G06F 19/3487 705/3 |
| 2015/0356270 A1* | 12/2015 | Devarakonda | G06F 19/00 705/3 |

OTHER PUBLICATIONS

Kitamura, et al., "Deep Semantic Mapping Between Functional Taxonomies for Interoperable Semantic Search," In Proceedings of the 3rd Asain Semantic Web Conference (ASWC 2008), LNCS 5367, Springer-Verlag, 2008, pp. 137-151.

Skupin, et al., "Visualizing the Topical Structure of the Medical Sciences: A Self-Organizing Map Approach," PLOS one, Visualizing the Medical Sciences, vol. 8, Issue 3, e58779, Mar. 2013, pp. 1-16.

IBM, "Method for Health Overview and Drill-Down Using Overlays," IP.com No. IPCOM000174799D, Sep. 24, 2008, pp. 1-6.

IBM, "A System & Method to Enable Pico-based Semantic Search on Clinical Evidence," IP.com No. IPCOM000190137D, Nov. 18, 2009, pp. 1-6.

Brown, et al., "VistA—U.S. Department of Veterans Affairs National-Scale HIS," International Journal of Medical Informatics, 69, 2003, pp. 135-156.

Mueller, K., Visual Analytics and Information Visualization in Healthcare, Computer Science, Lab for Visual Analytics and Imaging (VAI), Stony Brook University, Mar. 7, 2012, 53 pages.

Zhang, et al., "AnamneVis: A Framework for the Visualization of Patient History and Medical Diagnostics Chains," Proceedings of the IEEE VisWeek Workshop on Visual Analytics in Healthcare: Understanding the Physicians Perspective, Oct. 23, 2011, pp. 1-4.

Zhang, et al., "A Visual Analytics Framework for Emergency Room Clinical Encounters," IEEE Workshop on Visual Analytics in Health Care, Salt Lake City, Oct. 2010, pp. 1-8.

Plaisant, et al., "LifeLines: Using Visualization to Enhance Navigation and Analysis of Patient Records," AMIA, Inc, 1998, pp. 76-80.

Kanayama, et al., "Answering Yes/No Questions via Question Inversion," Proceedings of COLING 2012: Technical Papers, Dec. 2012, pp. 1377-1392.

Chapman, et al., "A Simple Algorithm for Identify8ing Negated Findings and Diseases in Discharge Summaries," Journal of Biomedical Informatics, 34, May 29, 2001, pp. 301-310.

Wang, et al., "Relation Extraction with Relation Topics," Proceedings of the Conference on Empirical Methods in Natural Language Processing, Jul. 27-31, 2001, 11 pages.

Read, et al., "Sentence Boundary Detection: A Long Solved Problem?," Proceedings of COLING 2012: Posters, Dec. 2012, pp. 985-994.

Fan, et al., "Mining Knowledge from Large Corpora for Type Coercion in Question Answering," Web Scale Knowledge Extraction (WEKEX) Workshop at International Semantic Web Conference, 2011, 17 pages.

Clarke, et al., "Exploiting Redundancy in Question Answering," SIGIR'01, Sep. 9-12, 2001, 8 pages.

Prager, et al., "Question-Answering by Predictive Annotation," SIGIR 2000, 2000, pp. 184-191.

Moldovan, et al., "The Structure and Performance of an Open-Domain Question answering System," In Proceedings of the Conference of the Association for Computational Linguistics, 2000, 8 pages.

Ferrucci, et al., "UIMA: An Architectural Approach to unstructured Information Processing in the Corporate Research Environment," To appear in a Special Issue of the Journal of Natural Language Engineering 2004, 2004, pp. 1-26.

Stephane M. Meystre et al., "Randomized controlled trial of an automated problem list with improved sensitivity", International journal of medical informatics 7 7 ( 2 0 0 8 ) 602-612.

Stephane M. Meystre et al., "Natural language processing to extract medical problems from electronic clinical documents: Performance evaluation", Journal of Biomedical Informatics 39 (2006) 589-599.

Stephane Meystre et al., "Automation of a problem list using natural language processing", BMC Medical Informatics & Decision Making Apr. 22, 2014. pp. 1-11.

Lise Poissant et al., "Assessing the accuracy of an inter-institutional automated patient-specific health problem list", BMC Medical Informatics and Decision Making 2010, 10:10 http://www.biomedcentral.com, 2010, pp. 1-10.

U.S. Appl. No. 14/300,699, Office Action Communication dated Aug. 3, 2016, pp. 1-21.

U.S. Appl. No. 14/300,699, Office Action Communication dated Feb. 7, 2017, pp. 1-24.

U.S. Appl. No. 14/300,699, Advisory Action dated Apr. 13, 2017, pp. 1-4.

U.S. Appl. No. 14/300,699, Office Action Communication dated Dec. 14, 2017 pp. 1-29.

U.S. Appl. No. 14/300,699, Notice of Allowance dated Jul. 13, 2018 pp. 1-6.

* cited by examiner

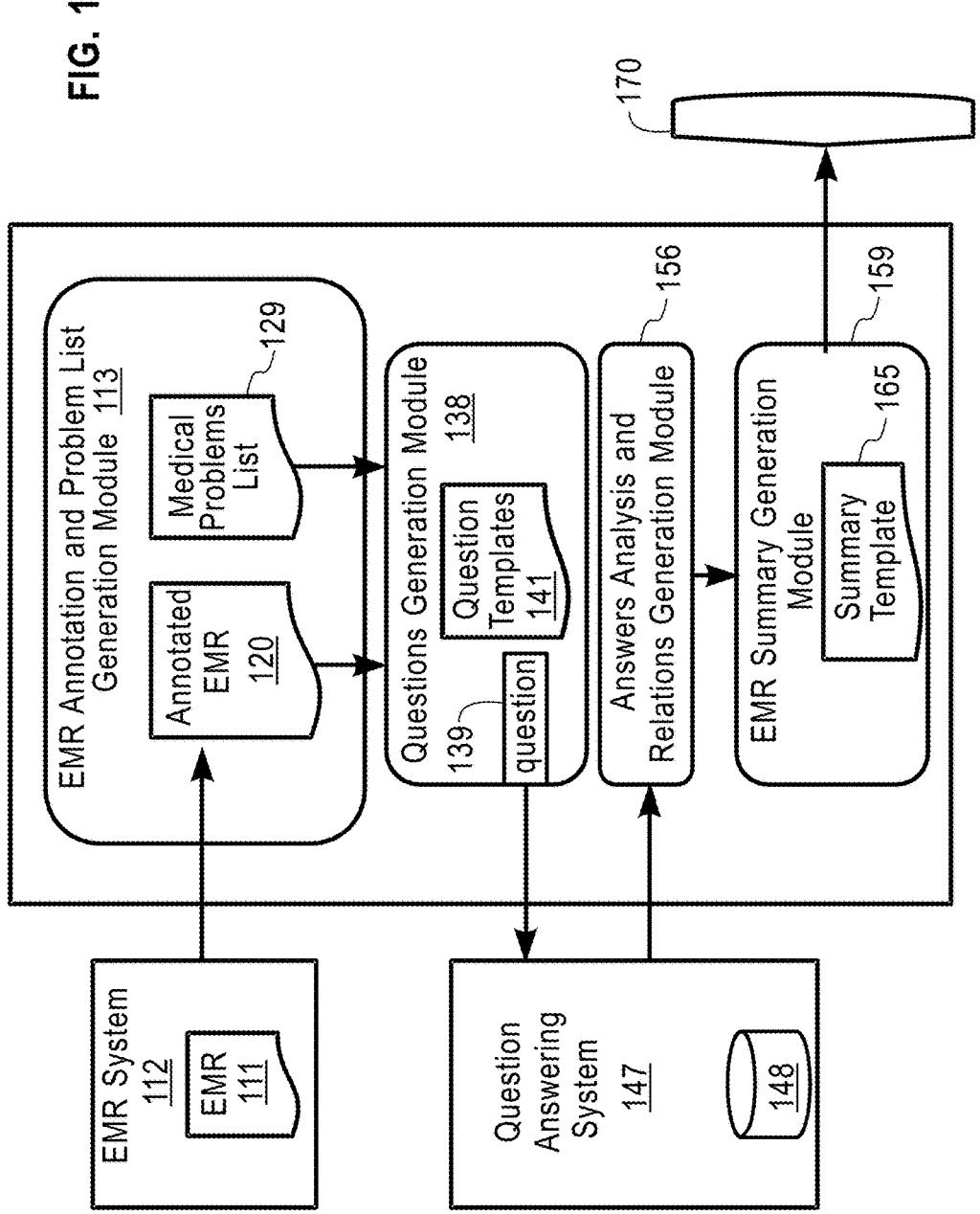

| Problem | Substance Name | Score |
|---|---|---|
| Hyperlipidemia | EPHEDRINE SULFATE | 0.06 |
| Hyperlipidemia | THIOPENTAL | 0.01 |
| Hyperlipidemia | HYDROMORPHONE | 0.01 |
| Hyperlipidemia | DIPHENHYDRAMINE | 0 |
| Hyperlipidemia | HYDROCHLOROTHIAZIDE | 1 |
| Hyperlipidemia | LISINOPRIL | 0.8 |
| Hyperlipidemia | ATORVASTATIN | 1 |
| Hyperlipidemia | AMLODIPINE | 1 |
| Hyperlipidemia | ZITHROMAX | 0 |
| Hyperlipidemia | ALBUMIN, HUMAN | 0 |
| Hyperlipidemia | BACTRIM DS | 0.01 |
| Hyperlipidemia | GUIATUSS DAC | 0 |
| Sinusitis | MAGNESIUM SULFATE | 0.02 |
| Sinusitis | FLONASE | 0.5 |
| Sinusitis | METHYLPREDNISOLONE | 0.3 |
| Sinusitis | ZOCOR | 0 |
| Sinusitis | TRIAMCINOLONE ACETONIDE | 1 |
| Sinusitis | DROPERIDOL | 0 |
| Sinusitis | POTASSIUM | 0.01 |
| Sinusitis | ALBUTEROL SULFATE | 0.3 |
| Sinusitis | SODIUM BICARBONATE | 0.15 |
| Chronic Obstructive Airway Disease | CLOTRIMAZOLE | 0 |
| Chronic Obstructive Airway Disease | DEXTROSE | 0 |
| Chronic Obstructive Airway Disease | IPRATROPIUM | 1 |
| Chronic Obstructive Airway Disease | DROPERIDOL | 0.06 |
| Chronic Obstructive Airway Disease | POTASSIUM | 0 |
| Chronic Obstructive Airway Disease | ALBUTEROL SULFATE | 1 |
| Chronic Obstructive Airway Disease | SODIUM BICARBONATE | 0.23 |
| Chronic Obstructive Airway Disease | KLOR-CON | 0 |
| Chronic Obstructive Airway Disease | COMBIVENT | 0.08 |
| Chronic Obstructive Airway Disease | HYDROCORTISONE | 1 |
| Chronic Obstructive Airway Disease | ATROPINE | 0 |
| Kidney Diseases | PSYLLIUM | 0.12 |
| Kidney Diseases | VANCOMYCIN | 0 |
| Kidney Diseases | HYDROMORPHONE | 0.01 |
| Kidney Diseases | DIPHENHYDRAMINE | 0.2 |
| Kidney Diseases | HYDROCHLOROTHIAZIDE | 0.98 |
| Kidney Diseases | LISINOPRIL | 1 |
| Kidney Diseases | SODIUM | 0 |

FIG. 2

| | antiemetics | antirheumatics | chemo therapeutics | dermatological agents | gastrointestinal medications | glucocorticoids | immuno suppressants |
|---|---|---|---|---|---|---|---|
| METHOTREXATE | | 1 | 1 | 1 | | | 1 |
| NASONEX | | 1 | | 1 | | | 1 |
| PREDNISONE | | 1 | | | 1 | 1 | 1 |
| DEXAMETHASONE | 1 | 1 | | | 1 | 1 | 1 |
| MEDROL | 1 | 1 | | 1 | | 1 | 1 |
| COMPAZINE | 1 | | | | 1 | | |
| DOLASETRON | 1 | | | | 1 | | |
| KYTRIL | 1 | | | | 1 | | |

```
<?xml version="1.0" encoding="utf-8"?>
<emraUITemplate>

<aggregatesSection>
<problemsList position="TopLeft">
  <renderer>com.ibm.emra.renderer.ProblemList</renderer>
  <event action="select">problemMedications, problemsLabs</event>
  <event action="deselect">problemMedications, problemsLabs</event>
  <event action="reset">problemMedications, problemsLabs</event>
</problemList>
<encounterTimeLine><renderer>com.ibm.emra.renderer.Encounters</renderer></encounterTimeLine>
<labValues><renderer>com.ibm.emra.renderer.LabValues</renderer></labValues>
<medications><renderer>com.ibm.emra.renderer.Medications</renderer></medications>
<allergiesAndSocial><renderer>com.ibm.emra.renderer.Medications</renderer></allergiesAndSocial>
</aggregatesSection>

<relationsSection>
<problemsMedications><provider>com.ibm.emra.relations.ProbsMeds</provider></problemsMedications>
<problemsLabs><provider>com.ibm.emra.relations.ProbsLabs</provider></problemsLabs>
</relationsSection>

</emraUITemplate>
```

FIG. 5

John Q. Smith, 47-year old male

301 — Problems
1. Hyperlipidemia
2. *Diabetes Mellitus*
3. Congestive Heart Failure
4. Sleep apnea
5. Crohn's disease 302 — Episodes of Care Timeline
- Primary Care
- Specialists
- Inpatient
- Nursing 303 — Lab Results
Creatinine 0.84 (10/30/2013)
Hemoglobin A1c 6.5 (10/18/2012)
LDL cholesterol 116 (10/30/2013)
Chloresterol 213 (10/30/2013)

304 — Medications
1. Metformin
2. Actos
3. Zocor
4. Plavix
5. Metoprolol
6. Purinethol 305 — Social History
1. Tobacco use: Yes
2. Drug use: No 306 — Allergies
1. Penicillin
2. Peanuts

FIG. 6

301 — Prob[lems]

1. Hyperlipidem[ia]
2. Diabetes Me[llitus]
3. Congestive H[eart]
4. Sleep apnea
5. Crohn's dise[ase]

303 — Lab Re[sults]

Creatinine
Hemoglobin A1c 6
LDL cholesterol 1
Chloresterol 2

Progress Note
Date: 11/07/2013

240.2 Diabetes Mellitus Type 2
H-A1c 7.1

272.4 Hyperlipidemia
Last Lipid Panel
CHOL 213
LDL 116
HDL 35

⎫
⎬ 309
⎭

SUBJECTIVE: patient with ongoing issues around his diabetic control. We have been fairly aggressively, upwardly adjusting his metformin. Despite frequent increases in his medication, he continues to have somewhat high blood A1c. What I cannot explain is why his A1c have not responded at all despite the increase in metformin. The staff reports to me that his appetite is good and that he is eating as well as ever. I talked to pt today. He feels a little fatigued. Otherwise, he is doing well.

PHYSICAL EXAMINATION: Vitals as in the chart. The patient is a pleasant and cooperative. He is in no apparent distress.

ASSESSMENT AND PLAN: Diabetes, still with some problematic blood A1c. To address this situation, I am going to introduce Actos. I will review the A1c again next month.

302

○ Primary Care
○ Specialists
◯◯◯ Inpatient
◯◯◯ Nursing

[ial] History — 305
use: Yes
: No

[A]llergies — 306

FIG. 7

ELECTRONIC MEDICAL RECORD SUMMARY AND PRESENTATION

BACKGROUND

The present disclosure relates to question-answering technology, and more specifically, to systems and methods for creating patient case summaries from electronic medical records (EMRs) using question-answering technology.

In the medical domain, a patient's medical conditions and treatment history are often stored in collection referred to as an electronic medical record (EMR). An EMR may include large volumes of plain text clinician notes, procedures performed along with results, structured data such as medications, and images such as CT scan images. An EMR may contain both structured and unstructured data resulting from a variety of medical care encounters of a patient with medical care providers. Examples of information that may be contained in an EMR include demographic information, family and social history, reports from care providers, procedures undergone, medications prescribed, diagnostic test results, vital signs, and administrative reports. Therefore, EMRs tend to be large; for example, an EMR of a single patient may contain hundreds of megabytes of structured and unstructured content. An aggregated clinical summary of patient information in the EMR is of high value in patient care if it shows the most important points relevant to patient care.

SUMMARY

Exemplary methods and computer program products herein (for outputting a clinical summary for a medical patient) receive an electronic medical record (EMR) for the medical patient, and extract medical data from the EMR. A list of medical problems relevant to the EMR is provided. These methods and computer program products identify relations between the medical problems and the medical data using a question-answering (QA) system and output the clinical summary for the EMR. The clinical summary comprises the list of medical problems, the medical data, and the relations.

Systems herein output a clinical summary for a medical patient. These systems comprise modules having program instructions embodied therewith. A receiving module of the modules receives an electronic medical record (EMR) for the medical patient and a list of medical problems. An extracting module of the modules extracts medical data from the EMR. A relation identification module of the modules identifies relations between the medical problems and the other medical data using a question-answering (QA) system. An outputting module of the modules, outputs the clinical summary for the EMR. The clinical summary comprises the list of medical problems, the medical data, and the relations.

BRIEF DESCRIPTION OF THE DRAWINGS

The systems and methods herein will be better understood from the following detailed description with reference to the drawings, which are not necessarily drawn to scale, and in which:

FIG. 1 is a schematic diagram illustrating process flow according to systems and methods herein;

FIG. 2 is an example of a template for creating an aggregated clinical summary page according to systems and methods herein;

FIG. 3 is an example of an aggregated clinical summary page according to systems and methods herein;

FIG. 5 is an example of medication clustering according to systems and methods herein;

FIG. 6 is an exemplary threshold chart according to systems and methods herein;

FIG. 7 is an illustration of a summary page according to systems and methods herein;

DETAILED DESCRIPTION

Figure 4:
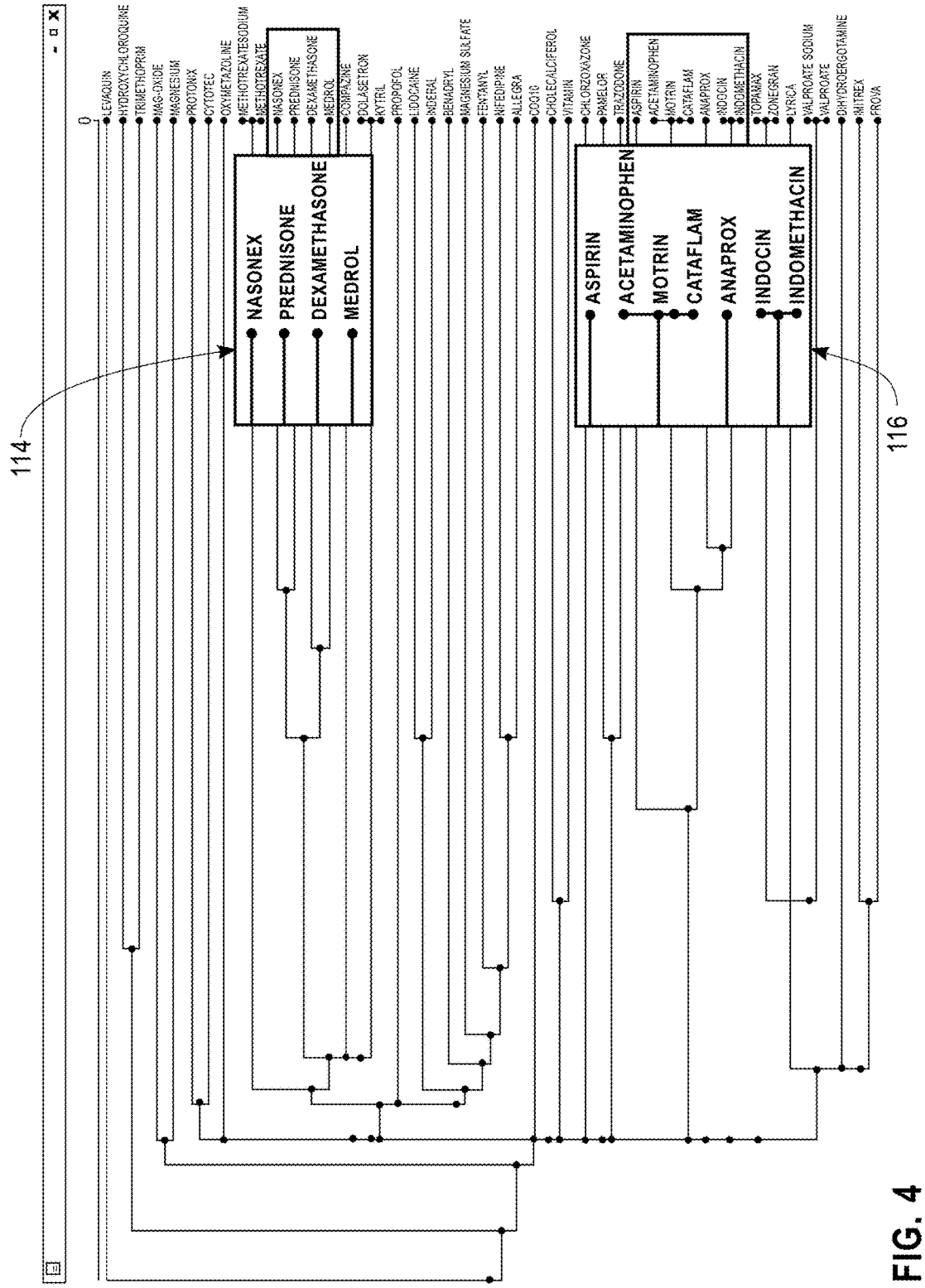
FIG. 4 is an example of a map of specific medications/problems to multiple general classes according to systems and methods herein.

It will be readily understood that the systems and methods of the present disclosure, as generally described and illustrated in the drawings herein, may be arranged and designed in a wide variety of different configurations in addition to the systems and methods described herein. Thus, the following detailed description of the systems and methods, as represented in the drawings, is not intended to limit the scope defined by the appended claims, but is merely representative of selected systems and methods. The following description is intended only by way of example, and simply illustrates certain concepts of the systems and methods, as disclosed and claimed herein.

The present invention enables creation of a case summary for presentation of a collection of unstructured case information. The present invention as described herein is directed to a specific embodiment of providing a case summary for a patient's Electronic Medical Record (EMR). However, the present invention is not limited to providing a case summary for an EMR, but can be extended to any collection of unstructured case information. Any collection of unstructured information that lends itself to being summarized based on a list of relevant entities can benefit from the present invention.

Generally, the present invention uses a list of entities of interest related to the case information, creates questions based on the list of entities of interest, enters the created questions into a question-answering (QA) system using an unstructured domain corpus, extracts case information summary entities based on the answers to those questions, outputs the list of entities of interest along with the case information summary entities, and indicates relationships between the entities of interest and the summary entities. The QA system can be any QA system capable of producing concise answers to given questions. However, the case summaries will vary in content and/or quality depending on the QA system used. A preferred QA system is the IBM Watson QA system, or instances of the IBM Watson system, developed by IBM and described with greater detail in the IBM Journal of Research and Development, Volume 56, Number 3/4,May/Jul 2012, the contents of which is hereby incorporated by reference in its entirety.

The present invention will be described in further detail with reference to a specific embodiment of the invention as used to provide a case summary based on a patient's EMR. With the advent of EMR systems, medical data is primarily captured and stored in a digital form. However, in many cases, the information is unstructured and the amount of information related to a single patient can easily range in the hundreds of megabytes. There is a need to present a summary of a longitudinal patient EMR (also referred to more broadly as case information) in order to assist a medical provider in providing medical care to the patient. The summary must be succinct, accurate, and show the most important data items from the EMR relevant to the patient's care.

Retrieving the most important data items from an EMR is difficult for a number of reasons. EMRs are typically very large, so maintaining summary information by hand can be extremely difficult. Moreover, simple keyword matching from a list of problems is insufficient, particularly in the medical field because it does not consider medical semantics. Furthermore, queries prepared in a semantic information retrieval language and run against a semantic database are dependent on formulating effective queries, which is not trivial.

Referring now to the specific embodiment of the present invention of creating a case summary for a patient's EMR as shown in FIG. 1. This embodiment of the present invention works by first obtaining a patient's EMR 111 from an EMR system 112 and analyzing the EMR in an EMR Annotation and Problem List Generation Module 113. The contents of the EMR 111 are analyzed using natural language processing techniques along with a medical ontology to recognize medical concepts within the EMR 111. The contents of the entries in the EMR 111 are annotated to identify the medical concepts and stored as an annotated EMR 120.

Natural language processing of the EMR 111 may use an ontology such as the Unified Medical Language System (UMLS). UMLS may be used in medical contexts to analyze clinical notes, such as the Clinical Text Analysis and Knowledge Extraction System (CTAKES). Certain text in an EMR may contain CUI (Concept Unique Identifier) fields. In these cases, a CUI search will yield results that exist within that concept. The EMR 111 may include structured data and unstructured data comprising, for example, demographics, family and social history, physician, nurse, and other care provider reports, procedures, medications, diagnostic test results, vital signs, and administrative reports.

In order to use lab findings and other numeric measurements in the medical domain, the system employs recognition capabilities incorporating context. For instance, a statement such as "320 mg/dL blood glucose" can use context to map to "Hyperglycemia." While in some cases this information may be associated with health records in structured form, in other cases the information is recorded as unstructured text. In one example, the present invention may provide a rule-based annotator that identifies measurements and test results as expressed in text. Based on existing guidelines, measurements are interpreted to be normal, high, or low, and mapped using general tables to the corresponding UMLS concept. Normal, high, and low values may also be expressed lexically (e.g. "elevated T4") and the methods can have trained statistical classifiers. Additionally, the methods may have collected a set of mapping rules to map to specific concepts in UMLS when they exist (e.g., mapping from "blood pressure is elevated" to the "Hypertension" concept).

In the methods herein, the contents of the EMR 111 have been annotated to identify medical concepts from the semantic features within the EMR 111 and syntactic features of the contents. A medical problem list 301 may be generated from the EMR 111 using named entity and relation annotators to extract clinical data. The clinical data may include signs, symptoms, findings, active and past diseases, current medications, allergies, demographics, social or family history, and many others. The concepts need to be broad enough to capture the descriptive intent of the clinician and interpret medical semantics. For example, hypertension to a clinician means "high blood pressure." Relations, for example, that indicate a specific family member had a particular disease, or that a symptom is mentioned in negation, need to be accurately captured from the language parse results. Laboratory test results need to be interpreted and evaluated for clinical significance. The extraction of this information from the patient's EMR provides context for generation of the medical problems list 301.

The present invention obtains a medical problems list 301 that can be entered manually by a medical professional, provided from an external source, or the list can be generated automatically from the medical data in the EMR 111 using the EMR Annotation and Problem List Generation Module 113. The preferred methodology for generating the problem list from the EMR for the present invention is described in greater detail in a related patent application entitled, "Automated Medical Problem List Generation from Electronic Medical Record," (IBM Docket YOR920140007US1) filed as U.S. patent application Ser. No. 14/300,699 and hereby incorporated by reference in its entirety.

After obtaining the patient's medical problems list 301, the present invention generates clinical data relationship questions 139 based upon the medical problems list 301 using a Questions Generation Module 138. Clinical data relationship questions 139 are generated for each item on the medical problems list 301. The clinical data relationship questions 139 are automatically generated using question templates 141 along with the entities in the medical problems list 301 and the medical concepts from the annotated EMR 120. The question templates 141 are pre-defined relation questions for categories of medical data that are commonly found in EMRs. Non-limiting examples of clinical data relationship questions include (1) "What medication treats [disease]", (2) "What medical condition is treated by [medications]", (2) "What clinical test should be considered for a family history of [family history entry]."

The question templates can include open-ended question formats or multiple-choice formats. For example, if the problems on a patient's medical problems list 301 included acute sinusitis, diabetes, and gastroesophageal reflux disease and a number of medications were identified from the annotated EMR 120 including glipizide, cataflam and fluticasone, then some non-limiting resulting clinical data relationship questions 139 may include: "What medication treats acute sinusitis, (a) glipizide, (b) cataflam, or (c) fluticasone?" and "What medical condition is treated by glipizide, (a) acute sinusitis, (b) diabetes, or (c) gastroesophageal reflux disease?" The question templates 141 are automatically selected and utilized based on the medical concepts in the annotated EMR 120.

After the clinical data relationship questions 139 are generated from the Questions Generation Module 138, the clinical data relationship questions 139 are entered into a question-answering (QA) system 147. The QA system uses a corpus of data 148 relevant to the domain to obtain answers to the clinical data relationship questions 139. The QA system is preferably a probabilistic QA system such as the IBM Watson QA system, or instances of the IBM Watson system, developed by IBM and described with greater detail in the IBM Journal of Research and Development, Volume 56, Number 3/4, May/July 2012.

Each of the clinical data relationship questions 139 is input to the QA system 147, which automatically searches the corpus of data 148, which can include structured and unstructured data, to retrieve answers to the clinical data relationship questions 139. The QA system 147 should be capable of analyzing natural language questions and generating candidate answers from unstructured text, however, the specific techniques used to produce the answers can vary. For example, QA system 147 may include multiple semantic search techniques, such as string matching, Latent Semantic Analysis (LSA) search, Logical Form Answer Candidate Scorer (LFACS) term matching, and relations-based search.

String matching may include an Indri search query built with the input question or search terms and run against the index or a structured data search string match within structured data fields. For example, Structured Term Recognition (STR) may recognize new terms of a specific type based on the structure of known terms for that type, e.g. "skin cancer" is a term and is a type of cancer.

An LSA search may incorporate pair-wise matching of each CUI from each note in the EMR, with all CUIs in the input. For example, LSA recognizes statistical association between two entities such as words, CUIs, or terms, based on their occurrence in the corpus, e.g. Hyperlipidemia and High Cholesterol are similar. High CUIs, and Notes with them are the matches. A similar match can be conducted with the structured data CUIs.

In LFACS term matching, each term from each Note may be semantically matched with terms from the clinical data relationship questions 139. Those Notes having a number of matches over a predetermined threshold may be kept. A similar match can be conducted with the structured data.

A relations-based search may use relations with the structured data to extract relevant passages, e.g. "simvastatin" in a query (matched with a CUI) may lead to CUIs in Notes through a "treats" relation.

Herein a description is provided with reference to the use of the IBM Watson QA architecture in the present invention. The QA system 147 (i.e. IBM Watson QA System) conducts a primary content specific search within a medical corpus for candidate answers and associated medically relevant notes, snippets, terms, and structured data. Once the search results are returned, the retrieved results are scored on a variety of measures of semantic match, medical relationship strength, and other criteria.

Candidate responses may be scored based on medical knowledge from medical corpora, including books, web pages, and other text-based knowledge representations. A score may be determined for the candidate responses based on the degree of semantic match of the passages to the clinical data relationship questions 139. Another score may be determined for the candidate responses based on the strength of medical relationship of the passages to the clinical data relationship questions 139. Additionally, the scores may be determined by how easily a candidate response may be "coerced" to the desired lexical answer type of the question. For additional information on this scoring technique please refer to the IBM Journal of Research and Development, Volume 56, Number 3/4, May/July 2012.

Answers are obtained from the QA system 147 based on the highest scoring candidate responses. After the answers and corresponding scores are obtained, the answers are analyzed in order to identify and record relationships between the medical problems and the medical data. For example, in FIG. 1, the answers are input into an Answers Analysis and Relations Generation Module 156 to extract relationship data between, for example, problems and medications and/or problems and laboratory test results, based on the answers provided by the QA system 147. The details of these analytics are described below.

FIG. 2 shows an example of relationship confidence scores 102 of different problems 104 returned by the QA system 147 for some clinical data relationship questions 139. For example, for a problem of "hyperlipidemia" identified from the patient's medical problems list 301, and an identified medication of "ephedrine sulfate" from the annotated EMR 120, the QA system 147 may identify a relationship score of 0.06. Based on this score, the systems and methods herein determine whether or not to record the medication as having a relationship to the problem based on a threshold value. This threshold value can be dependent on the type of relationship, and it can be determined by any method, but is preferably determined using machine learning techniques. For example, a machine learning technique can be used to determine what value of the score correctly predicts a valid relationship for a "is treated by" relationship. It's possible that a "is treated by" relationship requires a threshold score of at least 0.5 and therefore only "hydrochlorothiazide," "Lisinopril," "atorvastatin," and "amlodipine" are recorded as being related to the problem of "hyperlipidemia."

FIG. 3 shows an example of a relationship mapping 106 of specific medications 108 to related problems 110 according to systems and methods herein. Based on a threshold determination of a valid relationship as described in the paragraph above, the medical concepts in the medical problems list 301 are assigned a yes or no score (1 or 0) as being related to medical data from the EMR 111, such as medication, family history, lab results, etc. These relationships are stored and can be indicated in the EMR summary according to an embodiment of the present invention.

FIG. 4 shows how medical concepts can be grouped together 114 and 116 based on relationship similarities discovered from the QA system 147. For example, as described above, each medical concept may be recorded as having a valid relationship to problems as indicated by a yes or no score (1 or 0). If the number of relations is sufficiently large, then the medical concepts (in this case—medications) can be clustered based on their cosine similarity (i.e. correlation) using problem-relation vectors. Then medications in the same cluster, or even a "nearby" cluster, can be grouped together for filtering and organizing the information to be output. In other words, a vector of taxonomically reachable target classes is developed for each instance.

The Answers Analysis and Relations Generation Module 156 provides input to the EMR Summary Generation Module 159 that includes a summarization template 165, which may be used to determine which answers and relations to provide in the aggregated summary. FIG. 5 is an example of a template 118 for creating an aggregated clinical summary page according to systems and methods herein. After the answers are analyzed, the relations identified, and the entities grouped, the summarization template 165 may be used to determine which answers and relations to provide in the aggregated summary. The summarization template 165 may be customized by specifying the kinds of information to show. As shown in FIG. 5, the summarization template 165 may be built into software code or may be fixed.

An example of a template for use in a medical domain may provide for the rendering of the following types of information extracted from the EMR:
(1) Encounters and episodes timelines
(2) Generated list of problems
(3) Disease trajectories
(4) Active and inactive medications
(5) Family and social history
(6) Known allergies
(7) Important procedures
(8) Selected lab results
(9) Medical relationships among the clinical data.

FIG. 6 shows an example of an aggregated clinical summary (i.e. EMR summary) according to aspects of the present invention that will be shown on screen of a user's device 170 (e.g. laptop, PC, or tablet). The summary page may be arranged in discrete sections that show the medical problems list 301 as well as a clinical encounters timeline 302, laboratory test values 303, medications 304, social history 305, and allergies 306. In this example, the various clinical encounters 302 may be broken down into primary care, specialty, Inpatient, nursing, and other encounters. The aggregated clinical summary provides a problems-oriented summary of a longitudinal patient record that assists a physician by enabling rapid understanding of a patient's health and care management history. The aggregated clinical summary, as shown in FIG. 6, also provides indications of relationships between problems and the data in the other categories by highlighting, using colors, using symbols, or other appropriate methods.

Figure 8:
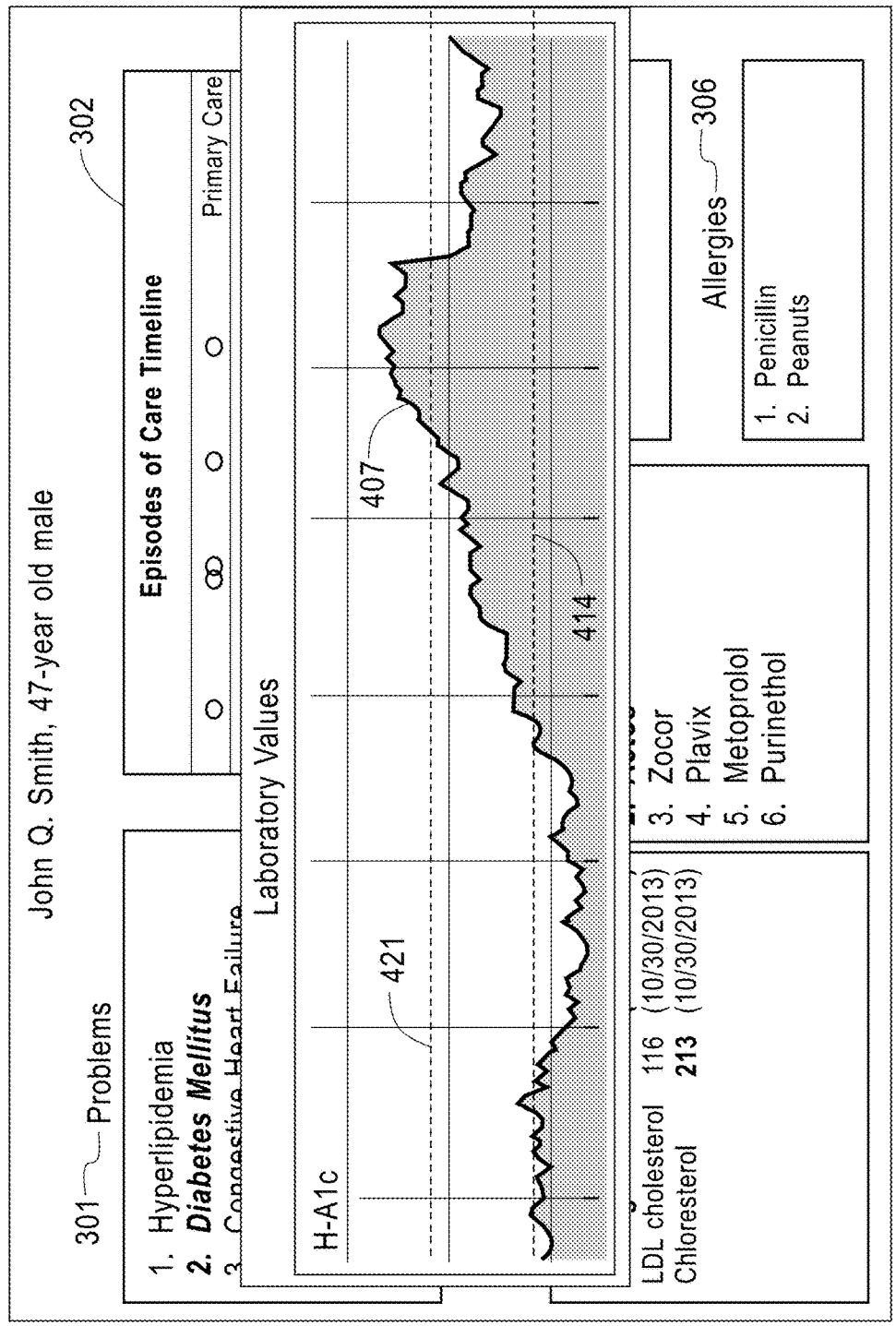
FIG. 8 is an illustration of a summary page showing a time-based trend graph according to systems and methods herein.

As shown in FIGS. 7 and 8, the EMR summary also provides for interaction by a user physician to drill down into more details (309) with respect to summarized information from the EMR. The ability to drill down to more details directly from the summary view enables rapid access to specific relevant medical information. First, as shown in FIG. 7, the drill down feature 309 provides access to the original clinical notes in the EMR. When the user physician selects a clinical encounter from the timeline in the summary view the clinical notes from that encounter are provided. Alternatively, as shown in FIG. 7, the user physician can be shown snippets of relevant information from the EMR with links to the full details. Second, as shown in FIG. 8, the clinical summary may present timelines of lab results 407 and medications enabling a view of care progression over time. In the example shown in FIG. 8, any of the laboratory test values 303 or medications 304 can be selected in order to show time-based trends of the lab values or medication amounts for the patient as well as preferred low value 414 and preferred high value 421.

Figure 9:
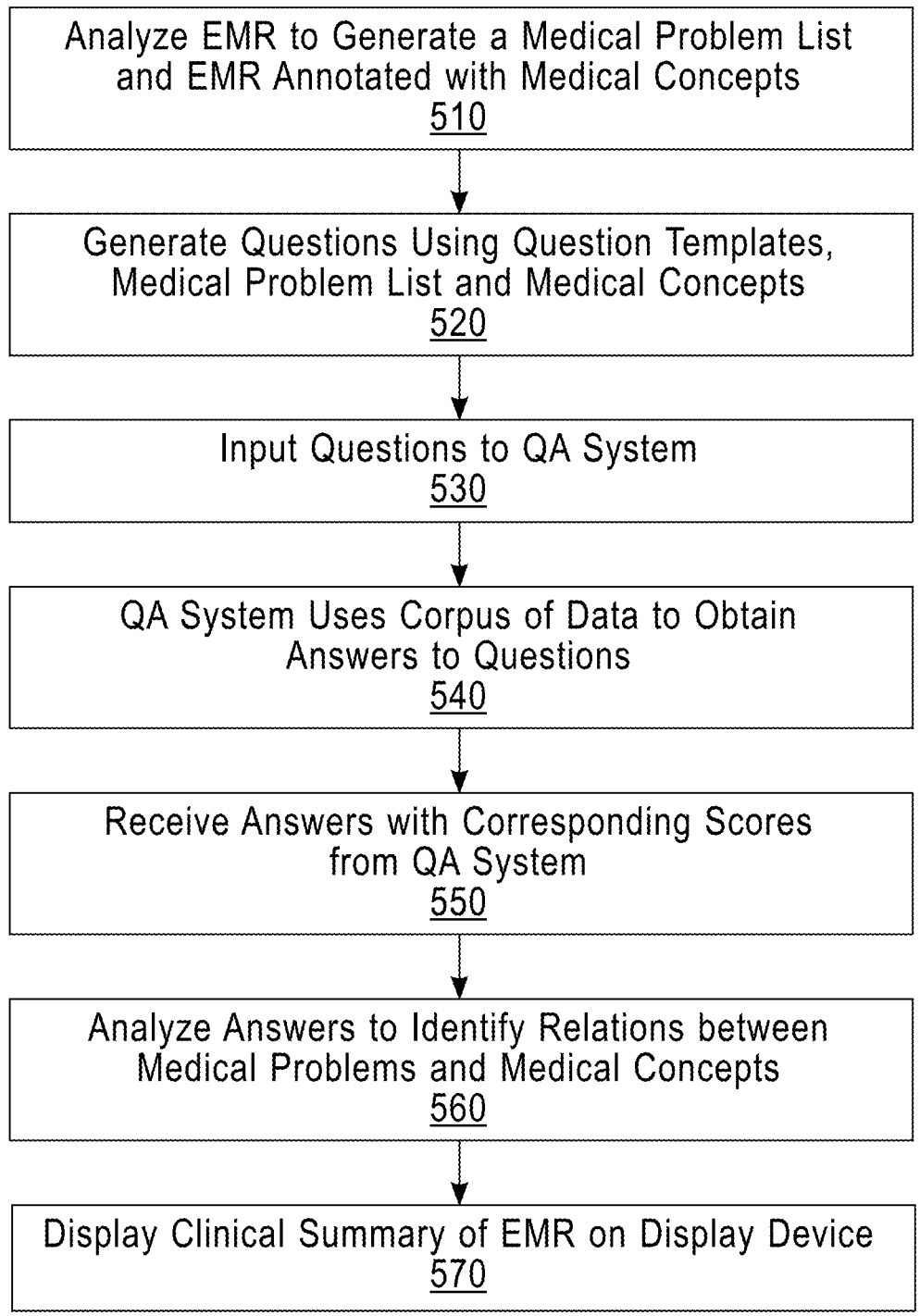
FIG. 9 is a flow diagram illustrating systems and methods herein.

FIG. 9 is a flow diagram illustrating the processing flow of an exemplary method according to systems and methods herein. In step 510, an EMR 111 is received and analyzed by a processor to generate a medical problem list 301 and an annotated EMR 120 including medical concepts identified within the EMR 111. In step 520, questions 139 are generated using question templates 141 along with the medical problem list 301 and the medical data from the annotated EMR 120. The questions 139 relate the data in the annotated EMR 120 to entities in the medical problem list 301, or data in the annotated EMR 120 to medical concepts in general. In step 530, the questions 139 are input into a question answering (QA) system 147, for example, IBM Watson. In step 540, the QA system 147 will generate answers to the questions by processing through a corpus of data 148, which may include unstructured information, for example, unstructured text. The corpus of data 148 may be maintained in at least one database separate from the electronic record. In step 550, the answers are received from the QA system 147 along with corresponding probabilistic scores indicating a degree of confidence/probability that the answers correctly answer the question. In step 560, the answers are analyzed to identify valid relations between the medical problems and medical data, or among medical concepts. The valid relations are based on the probabilistic scores and threshold values determined to identify a valid relation. In step 570, a clinical summary of the EMR 111 is output on the output device 170 for use by a medical provider. The clinical summary provides the medical data identified from the EMR 111 based on the relations to the medical problem list 301 and other medical data. The information output is based on a summarization template 165, the answers obtained and the corresponding scores. The information output includes representations of relations between the medical problems and the other medial data.

In a clinical setting, for example, the present invention can be used to develop a support tool that uses the context of an input case, a rich set of observations about a patient's medical condition, and generates a summary of medically relevant information indicating relations among the information with associated confidences based on searching and analyzing evidence from large volumes of content. Physicians and other care providers may more easily evaluate this vast amount of information along many different dimensions of evidence that can be extracted from a patient's EMR and other related content sources. For medicine, the dimensions of evidence may include symptoms, findings, patient history, social/family history, demographics, current medications, and many others. According to systems and methods herein, the output summary may include links back to the original evidence used to produce the summary and the confidence scores and supports the adoption of evidence-based medicine.

The aggregated clinical summary is succinct and accurate, and shows the most important points relevant to the patient's care. As described above, the summary output also enables the ability to drill down to the primary evidence (e.g. raw data) in order to see timelines, trajectories, and medically relevant relationships among the aspects of the patient care shown on the screen of a user's device 170 (e.g. laptop, PC, or tablet).

Figure 10:
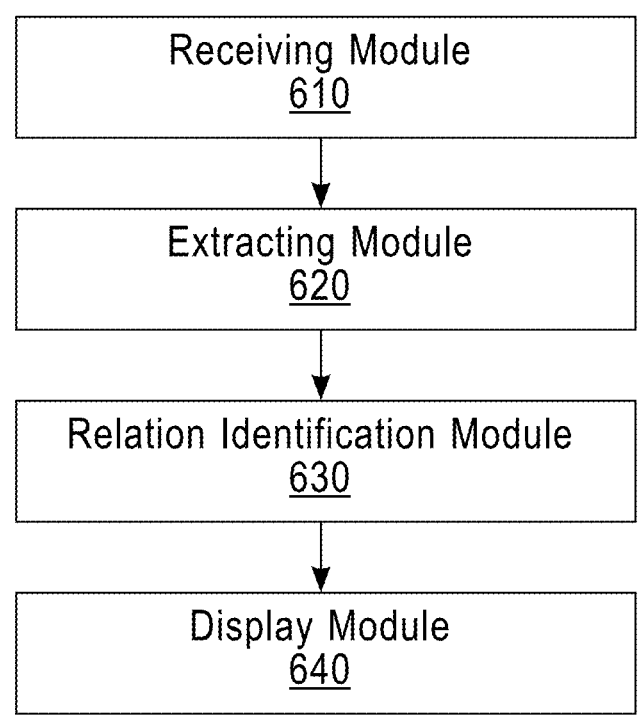
FIG. 10 is a schematic diagram illustrating modules of systems herein.

FIG. 10 illustrates exemplary systems herein that output a clinical summary for a medical patient. These systems comprise modules having program instructions embodied therewith. The modules are not a transitory signal per se, and the program instructions are executable by a computer, to perform a method. A receiving module 610 receives an electronic medical record (EMR) for the medical patient. An extracting module 620 extracts a list of medical problems and other medical data from the EMR. A relation identification module 630 identifies relations between the medical problems and other medical data using a question-answering (QA) system. An outputting module 640, outputs the clinical summary for the EMR. The clinical summary comprises the list of medical problems, the medical data, and the relations.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

In the on-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 10, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA)

bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 11:
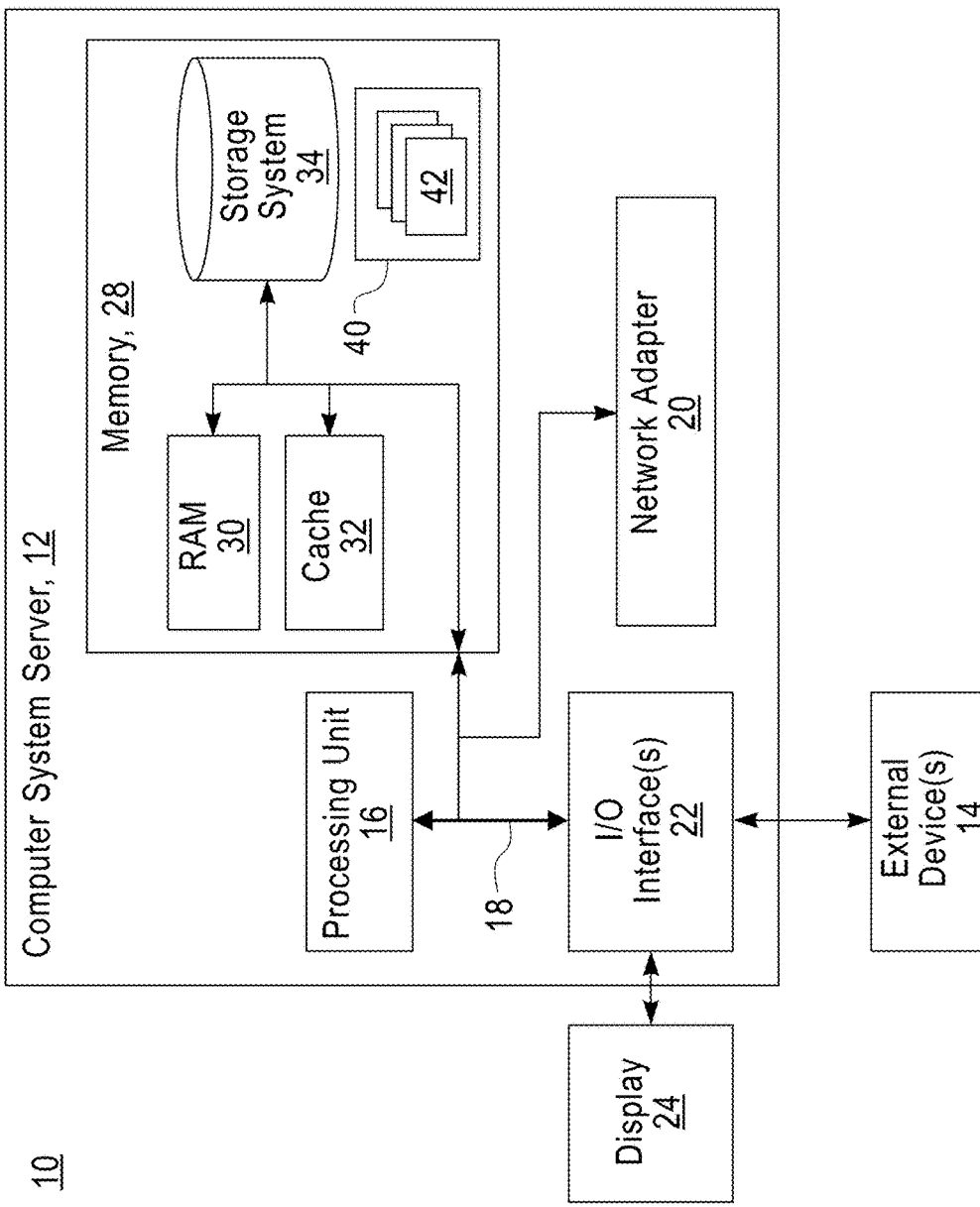
FIG. 11 is a schematic diagram of a hardware system according to systems and methods herein.

Referring now to FIG. 11, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 11 are intended to be illustrative only and that computing nodes 10 and cloud computing environment 50 can communicate with any type of computerized device over any type of network and/or network addressable connection (e.g., using a web browser).

Figure 12:
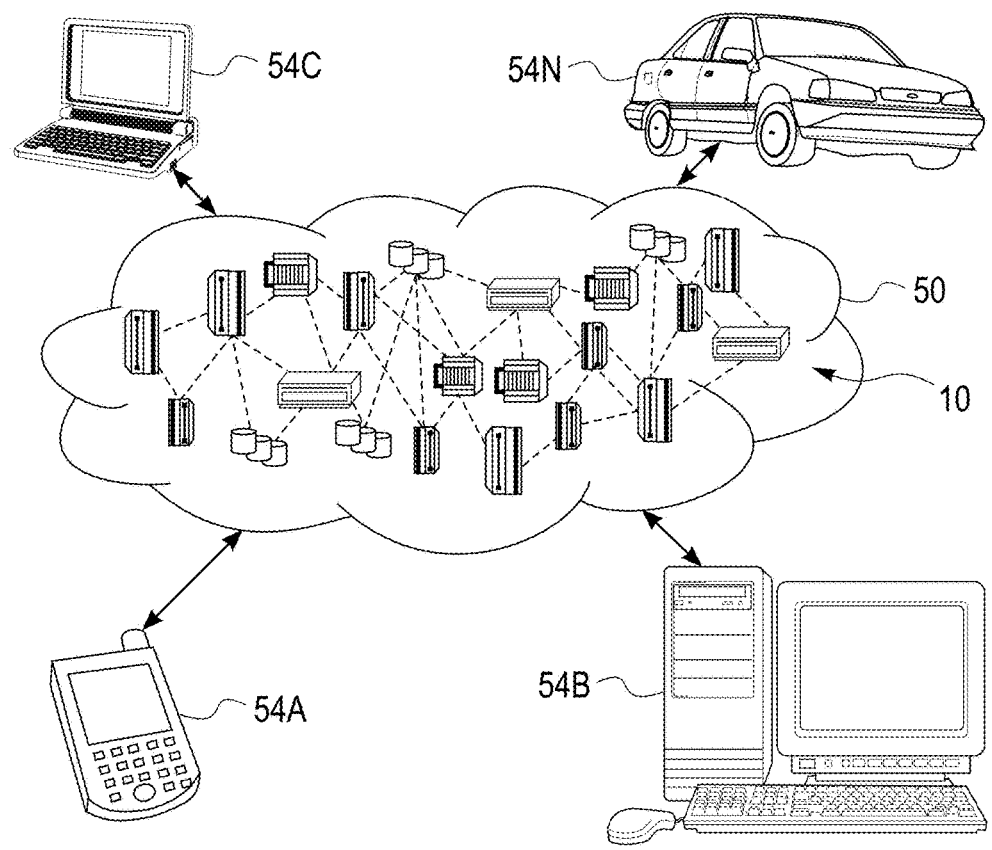
FIG. 12 is a schematic diagram of a computing environment according to systems and methods herein.
Figure 13:
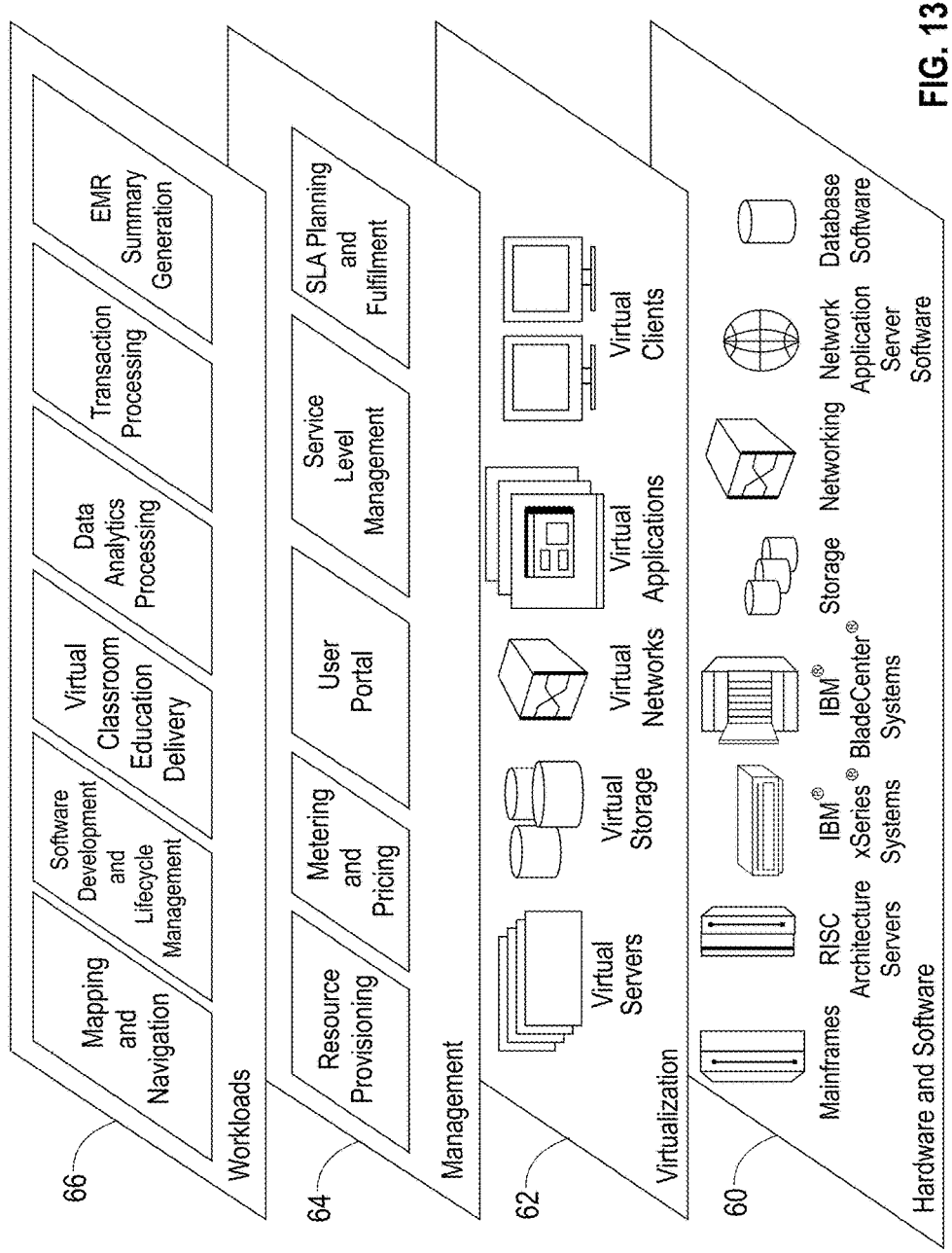
FIG. 13 is a schematic diagram of functional abstract layers according to systems and methods herein.

Referring now to FIG. 12, a set of functional abstraction layers provided by cloud computing environment 50 (FIG. 11) is shown. It should be understood in advance that the components, layers, and functions shown in FIG. 12 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; and EMR summary generation and presentation according to the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method of outputting a clinical summary for a medical patient, said method comprising:
    receiving, by a computer, an electronic medical record (EMR) for said medical patient from an EMR system, said EMR comprising structured data and unstructured data;
    analyzing, by said computer, said EMR using natural language processing techniques along with a medical ontology to recognize medical concepts within said EMR;
    mapping data from said EMR to standardized medical concepts in said medical ontology to identify medical problems of said medical patient associated with said EMR, using said computer;
    producing, by said computer, an annotated EMR by annotating contents of said unstructured data and said structured data to identify the medical concepts based on said mapping;
    extracting, by said computer, medical data from said annotated EMR using named entity and relation annotators based on standardized medical concepts;
    providing, by said computer, a list of medical problems contained in said annotated EMR;
    generating, by said computer, a clinical data relationship question for each medical problem on said list of medical problems based on said medical concepts using a question template based on a medical problem and said medical data extracted from said EMR;
    inputting, by said computer, each said clinical data relationship question into a question-answering (QA) system that uses natural language processing techniques, said QA system being separate from said EMR system and comprising a corpus of data having structured and unstructured data in a relevant medical domain, said corpus of data being maintained in at least one database separate from said EMR system;
    said QA system automatically searching said corpus of data to retrieve answers to the clinical data relationship question;
    said QA system obtaining an answer to each said clinical data relationship question and evidence profiles for each said answer, wherein said answer has a corresponding score indicating a degree of probability that the answer correctly answers the clinical data relationship question;
    analyzing, by said computer, each said answer;
    identifying, by said computer, whether a valid relation exists between said medical problem of said medical patient associated with said EMR and said medical data based on said score;
    said computer filtering out medical problems that have said score below a threshold;
    said computer creating a clinical summary for said medical patient associated with said EMR using a summarization template, said clinical summary comprising specific medical information for said medical patient comprising said list of medical problems, said medical data, and said relations;
    said computer prioritizing said clinical summary for said EMR based on said evidence profile and said score; and
    said computer outputting said clinical summary for said EMR.

2. The method according to claim 1, wherein said clinical summary further comprises sections containing medical concepts organized into categories.

3. The method according to claim 2, wherein said sections comprise laboratory test values, medications, and a timeline of clinical encounters.

4. The method according to claim 3, further comprising:
    receiving, by said computer, user interaction with a clinical encounter output in said timeline of clinical encounters; and
    said computer outputting information from said EMR related to said clinical encounter including content from a clinical note correlated to said clinical encounter.

5. The method according to claim 3, further comprising:
    receiving, by said computer, user interaction with a laboratory test value or a medication output in said clinical summary; and
    said computer outputting a timeline of values corresponding to said laboratory test values or amounts of medication.

6. The method according to claim 1, wherein said QA system comprises a probabilistic system that analyzes unstructured information and provides answers with scores indicating a degree of probability that the answers correctly answer the clinical data relationship question.

7. A system for outputting a clinical summary for a medical patient, said system comprising:
    an electronic medical record (EMR) system containing electronic medical records for a plurality of patients;
    a summary system connected to said EMR system; and
    a question-answering (QA) system connected to said summary system, said QA system being separate from said EMR system and comprising a corpus of data having structured and unstructured data in a relevant medical domain, said corpus of data being maintained in a database separate from said electronic medical records,
    said summary system comprising:
        a receiving module receiving an electronic medical record (EMR) for said medical patient and a list of medical problems from said EMR system, said EMR comprising structured data and unstructured data;
        an analysis module analyzing said EMR using natural language processing techniques along with a medical ontology to recognize medical concepts within said EMR, wherein said analysis module maps data from said EMR to standardized medical concepts in said medical ontology to identify medical problems of said medical patient associated with said EMR;
        an extracting module extracting medical data from said EMR using named entity and relation annotators based on standardized medical concepts, according to mapped data from said EMR, and annotating contents of said unstructured data and said structured data to identify the medical concepts to produce an annotated EMR containing a list of medical problems in said annotated EMR;

a relation identification module identifying relations between said medical problems in said annotated EMR and said medical data; and an outputting module;

said relation identification module generating a clinical data relationship question for each medical problem on said list of medical problems based on said medical concepts using a question template based on a medical problem and said medical data extracted from said EMR, said relation identification module inputting each said clinical data relationship question into said QA system, said QA system using natural language processing techniques and automatically searching said corpus of data to retrieve answers to the clinical data relationship question, said QA system obtaining an answer to each said clinical data relationship question and evidence profiles for each said answer, wherein said answer has a corresponding score indicating a degree of probability that the answer correctly answers the clinical data relationship question, said relation identification module analyzing each said answer using a summarization template to identify valid relations between the medical problems of said medical patient associated with said EMR and said medical data, said relation identification module identifying whether a relation exists between said medical problem and said medical data based on said score by filtering out candidate medical problems that have said score below a threshold to leave medical problem concepts of said medical patient, and said outputting module creating a clinical summary for said medical patient associated with said EMR comprising said list of medical problems, said medical data, and said relations, using said summarization template, prioritizing said clinical summary for said EMR based on said evidence profile and said score; and outputting said clinical summary for said EMR, wherein said clinical summary comprises said list of medical problems, said medical data, and said relations.

8. The system according to claim 7, wherein said clinical summary further comprises sections containing medical concepts organized into categories.

9. The system according to claim 8, wherein said sections comprise laboratory test values, medications, and a timeline of clinical encounters.

10. The system according to claim 9, said receiving module receiving user interaction with a clinical encounter output in said timeline of clinical encounters, and said outputting module outputting information from said EMR related to said clinical encounter including content from a clinical note correlated to said clinical encounter.

11. The system according to claim 9, said receiving module receiving user interaction with a laboratory test value or a medication output in said clinical summary; and said outputting module outputting a timeline of values corresponding to said laboratory test values or amounts of medication.

12. The system according to claim 7, wherein said QA system comprises a probabilistic system that analyzes unstructured information and provides answers with scores indicating a degree of probability that the answers correctly answer the clinical data relationship question.

13. A computer program product, said computer program product comprising a computer readable storage medium having program instructions embodied therewith, wherein the computer readable storage medium is not a transitory signal per se, the program instructions being executable by a computer, to perform a method of outputting a clinical summary for a medical patient comprising:

automatically, by said computer, receiving an electronic medical record (EMR) for said medical patient from an EMR system, said EMR comprising structured data and unstructured data;

automatically, by said computer, analyzing said EMR using natural language processing techniques along with a medical ontology to recognize medical concepts within said EMR;

automatically, by said computer, mapping data from said EMR to standardized medical concepts in said medical ontology to identify medical problems of said medical patient associated with said EMR;

automatically, by said computer, producing an annotated EMR by annotating contents of said unstructured data and said structured data to identify the medical concepts, based on said mapping;

automatically, by said computer, extracting medical data from said annotated EMR using named entity and relation annotators based on standardized medical concepts;

automatically, by said computer, providing a list of medical problems found in said annotated EMR;

automatically, by said computer, generating a clinical data relationship question for each medical problem on said list of medical problems based on said medical concepts using a question template based on a medical problem and said medical data extracted from said EMR;

automatically, by said computer, inputting each said clinical data relationship question into a question-answering (QA) system that uses natural language processing techniques, said QA system being separate from said EMR system and comprising a corpus of data having structured and unstructured data in a relevant medical domain, said corpus of data being maintained in at least one database separate from said EMR system;

said QA system automatically searching said corpus of data to retrieve answers to the clinical data relationship question;

said QA system obtaining an answer to each said clinical data relationship question and evidence profiles for each said answer, wherein said answer has a corresponding score indicating a degree of probability that the answer correctly answers the clinical data relationship question;

automatically, by said computer, analyzing each said answer;

automatically, by said computer, identifying whether a valid relation exists between said medical problem and said medical data based on said score;

automatically, by said computer, filtering out medical problems that have said score below a threshold;

automatically, by said computer, creating a clinical summary for said medical patient associated with said EMR using a summarization template, said clinical summary comprising specific medical information for said medical patient comprising said list of medical problems, said medical data, and said relations;

automatically, by said computer, prioritizing said clinical summary for said EMR based on said evidence profile and said score; and automatically, by said computer, outputting said clinical summary for said EMR.

14. The computer program product according to claim 13, wherein said clinical summary further comprises sections containing medical concepts organized into categories.

15. The computer program product according to claim 14, wherein said sections comprise laboratory test values, medications, and a timeline of clinical encounters.

16. The computer program product according to claim 15, further comprising:

receiving, by said computer, user interaction with a clinical encounter output in said timeline of clinical encounters; and said computer outputting information from said EMR related to said clinical encounter including content from a clinical note correlated to said clinical encounter.

17. The computer program product according to claim 15, further comprising:

receiving, by said computer, user interaction with a laboratory test value or a medication output in said clinical summary; and said computer outputting a timeline of values corresponding to said laboratory test values or amounts of medication.

* * * * *